United States Patent [19]

Allen et al.

[11] Patent Number: 4,834,024
[45] Date of Patent: May 30, 1989

[54] INDUCING POLYPLOIDY IN OYSTERS

[75] Inventors: Standish K. Allen; Jonathan A. Chaiton; Sandra L. Downing, all of King County, Wash.

[73] Assignee: Board of Regents of the University of Washington, Seattle, Wash.

[21] Appl. No.: 647,963

[22] Filed: Sep. 6, 1984

[51] Int. Cl.[4] .............................................. A01K 61/00
[52] U.S. Cl. ...................................................... 119/4
[58] Field of Search ................................... 119/2, 3, 4

[56] References Cited

U.S. PATENT DOCUMENTS 4,489,674 12/1984 Wolters et al. ........................ 119/3

OTHER PUBLICATIONS

Growth of American Oysters Increased by Polyploidy Induced by Blocking Meiosis but not Meiosis II, Aquaculture, Jon G. Stanley, H. Hidu and S.K. Allen, Jr., Aquaculture, 37, (1984), 147–155.

Amoeboid Movement at High Hydrostatic Pressure, Douglas A. Marsland and Dugald E. S. Brown, pp. 167–178.

Genetic Engineering by the Manipulation of Chromosomes, C. E. Purdom, Aquaculture, 33, (1983), 301–309.

Primary Examiner—Robert P. Swiatek
Attorney, Agent, or Firm—Seed and Berry

[57] ABSTRACT

A method of inducing polyploidy in oysters through the use of hydrostatic pressure is disclosed. The method includes separating oysters from one another such that male oysters are separated from female oysters, inducing the oysters to spawn, controlling the temperature of eggs from the oysters, fertilizing the eggs with sperm to form zygotes and then subsequently applying hydrostatic pressure to the zygotes to induce polyploidy.

10 Claims, 1 Drawing Sheet

INDUCING POLYPLOIDY IN OYSTERS

TECHNICAL FIELD

The present invention relates to the production of polyploid animals in general, and more specifically, to a method of inducing polyploids in oysters through the use of hydrostatic pressure.

BACKGROUND OF THE INVENTION

It has been known for many years that hydrostatic pressures can induce regression of cleavage furrows in dividing eggs (Marsland, D. A. and Brown, D. E. S. J. Cell and Comp. Physiol. 8: 167, 1936). Preliminary investigations with hydrostatic pressures involved a study of the movement of chromosomes by slowing or inhibiting them with hydrostatic pressures, while later studies used pressure to inhibit cell divisions to produce triploid animals, although purely for experimental purposes.

Beginning with work involving plaice (Purdom, C. E., Heredity 29: 11-24, 1972), many studies have examined methods to induce triploidy in economically important animals. A limited number of these studies have involved the use of hydrostatic pressure to induce triploidy in a variety of fish species while others utilized antibiotics to induce triploidy in shell fish.

It is possible to obtain triploids because of the nature of meiosis in lower animals. During meiosis, gametogenic cells undergo a duplication and subsequent division of the chromosomes. In some shellfish, two polar bodies are extruded following fertilization of the eggs. This extrusion can be inhibited by chemical or physical means. Consequently, an extra chromosome set from the polar body may be withheld within the oocyte. This extra set is retained within the egg in conjunction with the set obtained from the sperm, thus producing a triploid embryo.

Triploids can have practical benefits in aquaculture. These benefits arise from the reproductive sterility that a triploid animal is expected to display. By circumventing the otherwise normal energy expenditure associated with maturation, ripening and spawning of gametes, triploids have been shown to surpass their diploid counterparts in growth and survival (Stanely, J. et al., Aquaculture 37: 147-155, 1984).

In the case of Pacific oysters, in particular *Crassostrea gigas*, limiting the reproductive potential can be especially significant. In general, quality oysters are characterized by high levels of glycogen, which add texture and flavor to the meat. During the breeding season, the market quality of the oyster deteriorates because glycogen is diverted into gamete production instead of being stored. Triploid, and therefore neutered oysters will have reduced potential for maturing.

Consequently, there exists a need in the art for a method of inducing polyploidy in oysters on a consistent and costs effective basis. The present invention fulfills this need, and further provides other related advantages.

DISCLOSURE OF THE INVENTION

Briefly stated, the present invention consists of a method of inducing polyploids, and in particular triploids, in oysters. Oysters are first separated from one another such that male oysters are isolated from female oysters. Subsequently, the oysters are induced to spawn. While controlling the temperature of the eggs produced by the females, the eggs are fertilized with sperm to form zygotes. Hydrostatic pressure is then applied to the zygotes to induce polyploidy. The polyploid zygotes are subsequently cultivated through various means to form larvae and later mature oysters.

Utilizing this general method, approximately 30% triploidy may be obtained. When the eggs are maintained at approximately 25° C. and pressures of approximately 6000 to 10,000 psi are employed, the pressure is applied approximately 15 minutes after fertilization for a duration of 15 minutes.

Triploid oysters may be obtained via the use of hydrostatic pressure at other temperatures if the timing of pressurization coincides with the formation of polar bodies.

Although it is possible to induce polyploidy using pressures greater than 6000 to 10,000 psi, it is preferable to remain within this range due to the higher mortality rates exhibited when higher pressures are used.

BEST MODE FOR CARRYING OUT THE INVENTION

Figure 1:
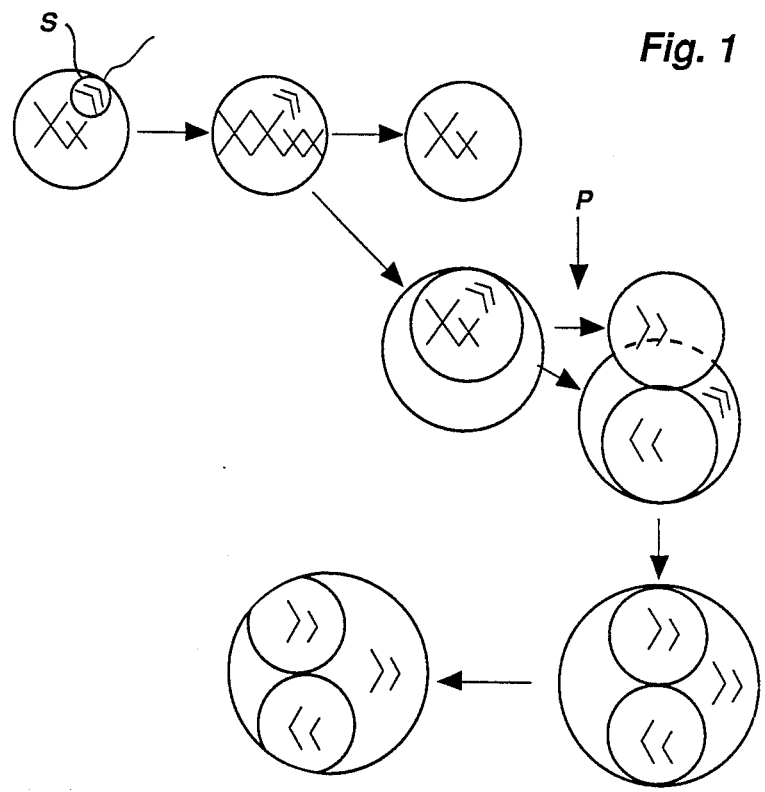
FIG. 1 is a diagrammatical representation illustrating the retention of a polar body by the method of the present invention.

In accordance with the present invention, polyploid animals are produced by applying hydrostatic pressure to the fertilized eggs of oysters. The time at which the pressure is applied coincides with the formation of the second polar body and is of sufficient degree to retain the second polar body within the egg. For purposes of the present invention as claimed herein, the term "polar body" is defined to include a cell that separates from an oocyte during meiosis.

The manipulation of chromosomes becomes feasible during the nuclear cycles of cell division by virtue of the organization of the chromosomes onto spindles. Changes to the number of chromosome sets may be brought about by the disruption of the spindle apparatus during meiosis. Suppressing metaphase prevents replicated chromosome sets from separating into daughter cells and may be achieved through the use of hydrostatic pressure.

When using hydrostatic pressure to induce triploidy in oysters, there are four important variables which must be controlled: (1) the temperature at which the procedure is conducted; (2) the time after fertilization at which the eggs are subjected to the pressure; (3) the amount of hydrostatic pressure; and (4) the duration of the treatment.

In general, the progress of meiosis within the pressure chamber is contingent on the first two variables. In light of this fact, it is essential to control the temperature of eggs obtained from the oysters in order to accurately time the application of the pressure to coincide with the formation of polar bodies.

Although a relatively wide range of pressures may be utilized, it is preferable to use pressures which fall between 6,000 and 10,000 psi due to the higher mortality rates exhibited when substantially higher pressures are used.

In order to induce the oysters to spawn, it may be necessary to condition the oysters, especially in the winter months, so that gametes are ripe (Loosanoff, U. L. and H. C. Davis, Rearing of Bivalve Mollusks. In *Advances in Marine Biology* Vol. 1: 1–136; F. S. Russel, Ed., Academic Press, N.Y., 1936).

In addition, it is preferable to clean the oyster shells with 10% chlorine solution and remove any plants or animals which may adhere thereto to reduce bacterial contamination during incubation.

One method of separating male oysters from female oysters is to place the oysters individually into glass specimen or Pyrex dishes. The dishes should contain enough filtered sea water, preferably at a temperature of 28° C. to 32° C., to cover the oyster. Generally, 750 ml of sea water will be sufficient to cover the oyster. Isolation is necessary to keep the eggs which will be released from the females from becoming fertilized.

If the oysters do not spawn, there are a variety of suitable methods which may be used to induce the oysters to spawn. (Lanaan, J. E., Aquaculture 21: 323–336, 1980). Among these methods are thermal shock, the addition of micro algae, the addition of inviable sperm, or chemical inducement through the use of hydrogen peroxide or potassium chloride (Beattie, J. H. & K. K. Chu, Shellfish Hatchery Management Laboratory Manual; College of Fisheries, University of Washington, 1983). The sperm may be rendered inviable either by freezing or boiling.

In order to fertilize approximately 20 million eggs which have been released from a female, it is generally sufficient to use approximatley 2–3 ml of sea water from a dish containing a male oyster which has released its sperm.

After the eggs have been fertilized with sperm, a hydrostatic pressure apparatus is used to generate sufficient pressure to retain the second polar body within the fertilized egg.

Suitable pressure chambers may be easily acquired as stock items and can be adapted for use as a hydrostatic device to pressurize marine eggs. For example, equipment which may be readily adapted for use with oyster eggs may be obtained from High Pressure Equipment Company, Erie, Pa. Hydraulic presses which are typically used to bring the vessel to the desired pressure may be hand or electrically operated. Suitable hand presses which will generate the required pressures may be obtained from Enerpac, Butler, Wis. It is also possible to have a custom device built which could accommodate specific volumetric needs.

To summarize the example which follows, after male oysters have been separated from female oysters, the oysters are induced to spawn. The temperature of the eggs is then raised or lowered by placing the flask containing the eggs in a warm water bath if the temperature is too low or in a cold pack if the temperature is too high. When the desired temperature is reached, the eggs are fertilized through the addition of an adequate quantity of sperm (S).

Hydrostatic pressure (P) is then applied to the fertilized eggs or zygotes to induce triploidy through retention of a polar body as shown in FIG. 1 and the triploid zygotes are subsequently cultivated following standard bivalve culture techniques (Loosanoff, U. L. and H. C. Davis, Rearing of Bivalve Mollusks. In *Advances in Marine Biology* Vol. 1: 1–136; F. S. Russel, Ed., Academic Press, N.Y., 1936).

The following example is offered by way of illustration and not by way of limitation.

EXAMPLE

Oysters which had been conditioned so that the gametes were ripe and the oysters would spawn were placed individually in glass Pyrex dishes with enough filtered sea water (temperature; 28° C. to 32° C.) to cover the oyster. The oysters were then induced to spawn by rapidly raising the temperature of the water surrounding the oyster. Unfertilized eggs were then siphoned from the glass dishes into a 2 liter flask using a $\frac{3}{8}''$ plastic hose. This method prevents any sperm which may be on the outside of the glass dish from being transferred to the 2 liter flask, thus avoiding contamination. A sperm-free thermometer was then used to monitor the temperature of the unfertilized eggs. The flask was placed in a water both of approximately 50° C. and the temperature of the unfertilized eggs constantly checked while raising the temperature of the eggs to 25° C. When the desired temperature was reached, the flask was removed from the water bath.

Enough sperm (2 ml at an optical density of 20 on a Chemtrix type 24 colorimeter) was added to the flask to adequately fertilize approximately 20 million eggs. At this stage a time clock was initiated, using "time of fertilization" as "time equals 0."

Figure 2:
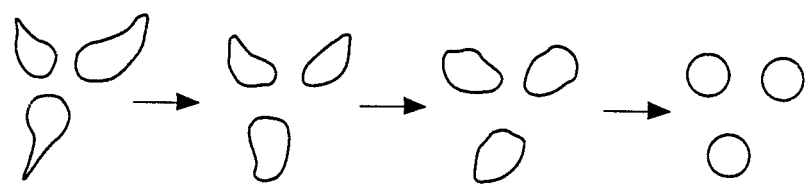
FIG. 2 is a series of illustrations showing the developmental changes in the shape of an oyster egg after fertilization.

A few drops of the fertilized egg solution was placed on a standard microscope slide under lower power (10×) to observe the slight developmental changes in the egg shape. After the "rounding of the egg" had occurred as shown in FIG. 2, the fertilized egg solution was poured into the pressure chamber, making sure that the chamber was entirely filled with the solution. This normally occurs when approximately 10 minutes have elapsed since "time equal 0." The chamber was then properly sealed.

The pressure chamber was then brought to the desired hydrostatic pressure (6500 psi) when time equaled approximately 15 minutes. The desired pressure must be obtained within a few seconds to ensure that development of the egg or zygote does not proceed into the extrusion of a polar body from the egg. The pressure should be monitored and maintained as necessary.

Figure 3:
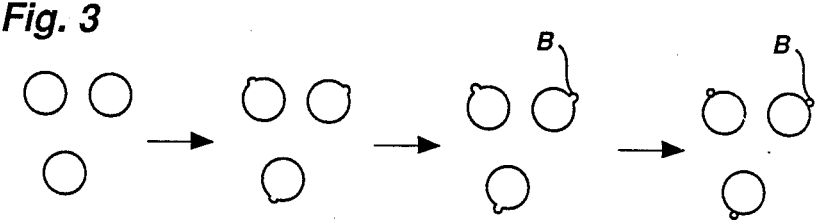
FIG. 3 is a series of illustrations showing the emergence and formation of a polar body from an egg.

When a majority of the eggs which are being monitored under the compound microscope produced polar bodies (B) as shown in FIG. 3, generally when time equals 30 minutes, the pressure was released, the lid removed, and the fertilized eggs carefully poured into a clean 2 liter flask. The fertilized eggs or zygotes were then placed in a rearing tank and cultivated using standard hatchery procedures.

Utilizing this general method, approximately 30% triploidy were obtained as determined by cytofluorometric analysis (Chaiton J. A. et al. Proc. Natl. Shellfish Assoc., September 1984) which allows for the unambiguous indentification of the ploidy of every individual.

The triploid oysters were viable and the extra DNA physiologically tolerated, resulting in oysters which will be characterized by improved texture and flavor.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of inducing polyploidy in oysters, comprising:

separating oysters from one another such that male oysters are isolated from female oysters;

inducing said oysters to spawn;

controlling the temperature of eggs from said oysters;

fertilizing said eggs with sperm to form zygotes;

applying hydrostatic pressure to said zygotes at a predetermined intensity for a predetermined duration after a predetermined time following formation of said zygotes to induce polyploidy; and cultivating said polyploid zygotes.

2. The method of claim 1 wherein the application of pressure coincides with the formation of polar bodies within said eggs.

3. The method of claim 1 wherein said oysters are induced to spawn through thermal shock, addition of micro algae, or the addition of inviable sperm.

4. The method of claim 1 wherein said pressure is between 6000 and 10,000 psi.

5. The method of claim 4 wherein said temperature is controlled at approximately 25° C. and said pressure is applied approximately 15 minutes after fertilization.

6. The method of claim 5 wherein said pressure is applied for approximately 15 minutes.

7. The method of claim 1 wherein approximately 2 ml of sperm containing fluid with an optical density of 20 is added to approximately 20 million eggs to fertilize said eggs.

8. A method of inducing polyploidy in oysters, comprising:

separating oysters from one another such that male oysters are isolated from female oysters;

inducing said oysters to spawn;

controlling the temperature of eggs from said oysters at approximately 25° C.;

fertilizing said eggs with sperm to form zygotes;

applying hydrostatic pressure of approximately 6000 to 10,000 psi for a predetermined duration approximately 15 minutes after fertilization to said zygotes to induce polyploidy; and cultivating said polyploid zygotes.

9. The method of claim 8 wherein said pressure is applied for approximately 15 minutes.

10. The method of claim 8 wherein approximately 2 ml of sperm containing fluid with an optical density of 20 is added to approximately 20 million eggs to fertilize said eggs.

* * * * *